United States Patent
Hsiao et al.

(10) Patent No.: US 10,231,863 B2
(45) Date of Patent: Mar. 19, 2019

(54) METHOD OF ADJUSTING SNORING MOUTHPIECE

(71) Applicant: Soteria Biotech Co., Ltd., Taipei (TW)

(72) Inventors: Hung-Ta Hsiao, Taipei (TW); Ing-Hsien Lo, Taipei (TW)

(73) Assignee: SOTERIA BIOTECH CO., LTD., Taipei (TW)

( * ) Notice: Subject to any disclaimer, the term of this patent is extended or adjusted under 35 U.S.C. 154(b) by 330 days.

(21) Appl. No.: 15/371,439

(22) Filed: Dec. 7, 2016

(65) Prior Publication Data
US 2018/0055683 A1    Mar. 1, 2018

(30) Foreign Application Priority Data
Aug. 24, 2016 (TW) ............................. 105127140 A

(51) Int. Cl.
| *A61B 5/00* | (2006.01) |
| *A61B 5/08* | (2006.01) |
| *A61B 6/03* | (2006.01) |
| *A61F 5/56* | (2006.01) |

(52) U.S. Cl.
CPC ............... *A61F 5/566* (2013.01); *A61B 5/08* (2013.01); *A61B 5/4818* (2013.01); *A61B 5/4836* (2013.01); *A61B 6/032* (2013.01)

(58) Field of Classification Search
CPC ...... A61F 5/56; A61F 5/566; A61F 2005/563; A61B 5/08; A61B 5/082; A61B 5/0826; A61B 5/4806; A61B 5/4809; A61B 5/4818; A61B 5/4836; A61B 6/032
See application file for complete search history.

(56) References Cited

U.S. PATENT DOCUMENTS

| 7,794,399 B2 * | 9/2010 | Singh | A61B 5/085 600/443 |
| 2007/0183572 A1 * | 8/2007 | Drummond | A61F 5/566 378/98.8 |
| 2015/0007830 A1 * | 1/2015 | Remmers | A61F 5/566 128/848 |
| 2016/0128624 A1 * | 5/2016 | Matt | A61C 19/045 600/301 |
| 2016/0199216 A1 * | 7/2016 | Cam | A61F 5/566 128/848 |
| 2017/0135603 A1 * | 5/2017 | Hanewinkel | A61B 5/087 |
| 2017/0135850 A1 * | 5/2017 | Veis | A61F 5/566 |
| 2017/0143445 A1 * | 5/2017 | Abkai | A61B 90/39 |
| 2017/0156921 A1 * | 6/2017 | Brinker | A61F 5/56 |
| 2018/0353321 A1 * | 12/2018 | Veis | A61F 5/566 |

* cited by examiner

*Primary Examiner* — Kari K Rodriquez
(74) *Attorney, Agent, or Firm* — Juan Carlos A. Marquez; Marquez IP Law Office PLLC

(57) ABSTRACT

A method of adjusting a snoring mouthpiece includes the steps of: reading a first medical image, establishing a first respiratory tract model, performing a first respiration simulation, reading a second medical image, establishing a second respiratory tract model, performing a second respiration simulation, calculating an adjustment distance, and adjusting the snoring mouthpiece. The method is so designed that tomographic images of a patient's respiratory tract are read at two separate times in order to establish models, perform respiration simulations, and thereby provide the correct distance by which to adjust the snoring mouthpiece. This allows the snoring mouthpiece to be adjusted rapidly and correctly and work effectively.

10 Claims, 2 Drawing Sheets

METHOD OF ADJUSTING SNORING MOUTHPIECE

BACKGROUND OF THE INVENTION

1. Technical Field

The present invention relates to an adjustment system and more particularly to a method of adjusting a snoring mouthpiece.

2. Description of Related Art

With the advancement of daily life-related technologies, a great number of means or methods have been developed to treat breathing problems that occur during sleep. The treatment of snoring, in particular, has been viewed as an essential way to prevent sleep-related breathing disorders, including sleep apnea.

Many patients with sleep apnea have an apnea hypopnea index (AHI) as high as 50, meaning there could be 50 apnea and/or hypopnea events per hour of sleep. Doctors' recommended treatments for sleep apnea typically include anti-snoring surgery, anti-snoring orthopedic pillows, respirators, thermoplastic snoring mouthpieces, and custom-made snoring mouthpieces, in which custom-made mandibular advancement devices not only are a non-invasive, low-cost, and user-friendly alternative to surgery and the expensive (generally NT$80,000 to 90,000) and inconvenient respirators, but also are easy-to-manufacture and consistently effective.

Generally speaking, a custom-made snoring mouthpiece is configured to fine-tune the mandible while allowing proper occlusion. More specifically, such a mouthpiece advances, or pulls outward, the user's mandible and secures the mandible in this "protruded" position. The distance by which the mandible is to be advanced is adjusted on a regular basis by a dentist according to the user's jaw bones and the degree of base-of-tongue collapse. A custom-made snoring mouthpiece can be stably worn and can hold the user's teeth and tongue in place effectively, preventing them from obstructing breathing and sleeping.

As the fine-tuning method of most custom-made snoring mouthpieces is a trial-and-error process, which begins by assuming an effective value and makes subsequent adjustments according to the results of use, a user has to put up with numerous adjustments and all the discomfort incurred before the treatment is completed.

In light of the above, it will benefit those suffering from sleep apnea hugely if an innovative method is developed that can derive from only two sets of sequentially obtained imaging results or data the distance of mandibular advancement required by a custom-made snoring mouthpiece to prevent sleep apnea.

BRIEF SUMMARY OF THE INVENTION

The present invention relates to a method of adjusting a snoring mouthpiece by reading tomographic images of a patient's respiratory tract at two separate times and by establishing models and performing respiration simulations in order to provide the correct distance by which to adjust the snoring mouthpiece. This allows the snoring mouthpiece to be adjusted rapidly and correctly and work effectively.

The present invention provides a method of adjusting a snoring mouthpiece, wherein the method includes the steps of: reading a first medical image, or more particularly reading a first tomographic image of a patient's respiratory tract by a computation module; establishing a first respiratory tract model, or more particularly establishing the first respiratory tract model by the computation module according to the first tomographic image of the patient's respiratory tract; performing a first respiration simulation, or more particularly performing respiration simulation on the first respiratory tract model by the computation module in order to obtain a first respiratory pressure distribution, a first pressure difference, and a first jet angle; reading a second medical image, or more particularly reading a second tomographic image of the patient's respiratory tract by the computation module, wherein the second tomographic image is taken while the patient is holding an occlusal structure between his or her teeth; establishing a second respiratory tract model, or more particularly establishing the second respiratory tract model by the computation module according to the second tomographic image of the patient's respiratory tract; performing a second respiration simulation, or more particularly performing respiration simulation on the second respiratory tract model by the computation module in order to obtain a second respiratory pressure distribution, a second pressure difference, and a second jet angle; calculating an adjustment distance, or more particularly calculating a corrective advancement distance by the computation module according to the first respiratory pressure distribution, the first pressure difference, the first jet angle, the second respiratory pressure distribution, the second pressure difference, and the second jet angle; and adjusting the snoring mouthpiece, or more particularly adjusting the snoring mouthpiece according to the corrective advancement distance.

Implementation of the present invention at least involves the following inventive steps:

1. The snoring mouthpiece to which the present invention is applied can be manufactured by a simple process without using complicated equipment, thus lowering the costs of production and use.

2. Correct models of a patient's respiratory tract can be directly obtained rather than by trial and error.

3. The adjustment can be easily verified or confirmed to minimize errors in adjusting the snoring mouthpiece, thus saving time and expenses.

4. A precise corrective advancement distance can be obtained for the snoring mouthpiece.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art can easily understand the objects and advantages of the present invention by referring to the disclosure of the specification, the claims, and the accompanying drawings.

BRIEF DESCRIPTION OF THE SEVERAL VIEWS OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE INVENTION

Figure 1:
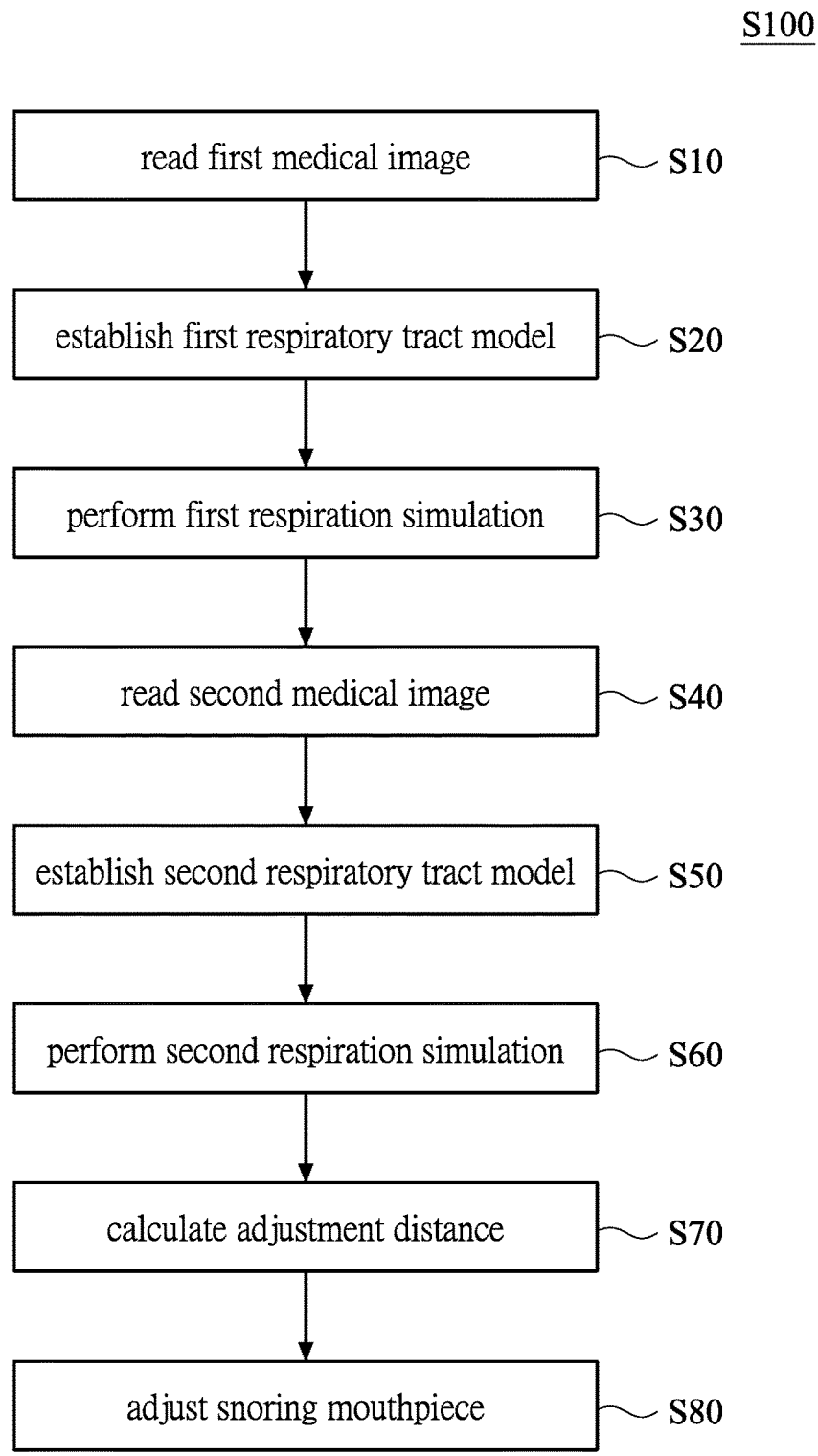
FIG. 1 is a flowchart showing the steps of the method in an embodiment of the present invention for adjusting a snoring mouthpiece.

According to an embodiment of the present invention, referring to FIG. 1, the method S100 of adjusting a snoring mouthpiece includes the steps of: reading a first medical image (S10), establishing a first respiratory tract model (S20), performing a first respiration simulation (S30), reading a second medical image (S40), establishing a second respiratory tract model (S50), preforming a second respiration simulation (S60), calculating an adjustment distance (S70), and adjusting the snoring mouthpiece (S80).

To carry out the step of reading the first medical image (S10) as shown in FIG. 1, a computation module reads a first tomographic image of a patient's respiratory tract. The first tomographic image may be an image taken by computed tomography (CT) or cone-beam computed tomography (CBCT).

The computation module may read the first tomographic image of the patient's respiratory tract through a direct connection, either wired or wireless, with a medical CT or CBCT device. Alternatively, the computation module may obtain the first tomographic image of the patient's respiratory tract by reading pre-stored image data generated by the CT or CBCT device.

The computation module may be a computer system installed with at least one computation or application program, a microprocessor system, a personal computer, a laptop computer, or a smart device.

To carry out the step of establishing the first respiratory tract model (S20) as shown in FIG. 1, the computation module establishes the first respiratory tract model according to the first tomographic image of the patient's respiratory tract in order for the model to correspond to the patient's respiratory tract. The first respiratory tract model may be a three-dimensional (3D) model of the patient's respiratory tract.

In one embodiment, the computation module employs a grayscale or numerical-value comparison method to acquire the position and shape of the patient's respiratory tract from the first tomographic image, in order to establish the first respiratory tract model according to the position and shape acquired.

To carry out the step of performing the first respiration simulation (S30) as shown in FIG. 1, the computation module performs respiration simulation on the first respiratory tract model to obtain data related to the patient's state of respiration, such as a first respiratory pressure distribution, a first pressure difference, and a first jet angle.

After that, referring to both FIG. 1 and FIG. 2, the step of reading the second medical image (S40) is carried out as follows. The computation module reads a second tomographic image of the patient's respiratory tract, wherein the second tomographic image is taken while the patient is holding an occlusal structure between his or her teeth. The occlusal structure may be a dental brace, an occlusal splint, an adjustable dental brace, or a highly elastic, adjustable occlusal splint 10.

Figure 2:
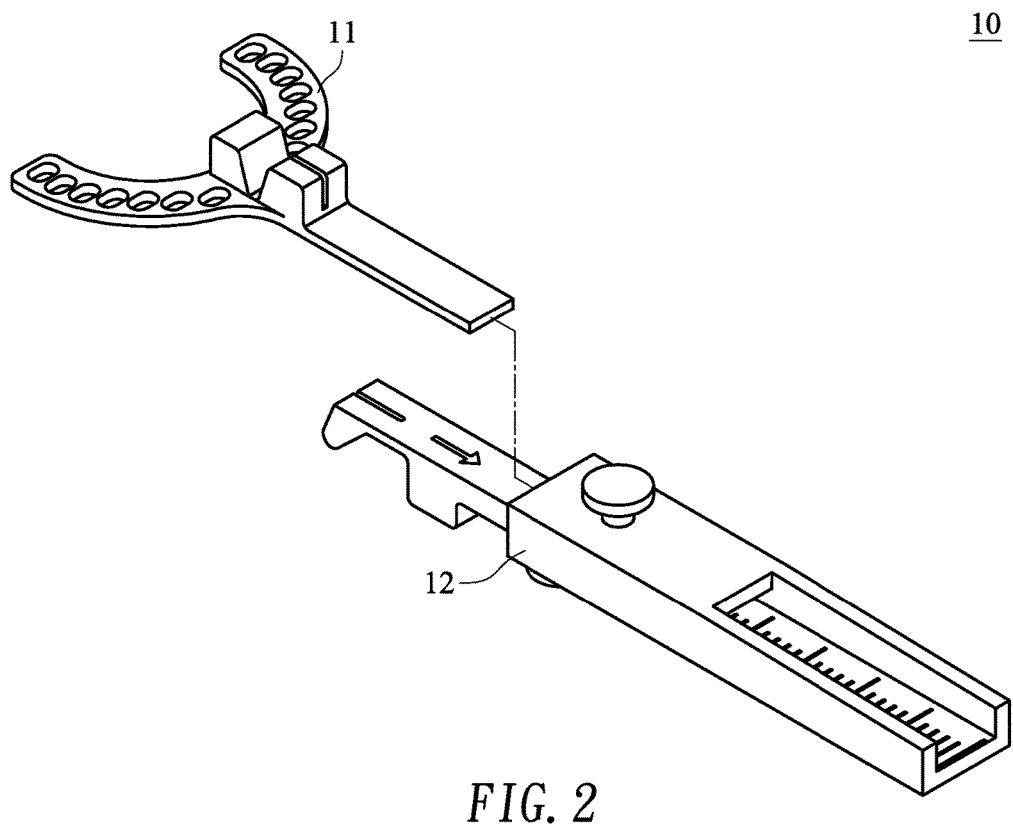
FIG. 2 is a perspective view of an adjustable occlusal splint for use in an embodiment of the present invention.

As shown in FIG. 2, the adjustable occlusal splint 10 includes an oral portion 11 and an adjusting portion 12. The oral portion 11 is configured to be held between the patient's teeth, and the adjusting portion 12, to adjust the position of the oral portion 11 in the patient's mouth.

The second tomographic image of the patient's respiratory tract may also be a CT or CBCT image. However, in order for the method S100 of adjusting the snoring mouthpiece to provide precise adjustment, the first and the second tomographic images must be of the same type, i.e., both being CT images or CBCT images.

To carry out the step of establishing the second respiratory tract model (S50) as shown in FIG. 1, the computation module establishes the second respiratory tract model according to the second tomographic image of the patient's respiratory tract so that the model corresponds to the patient's respiratory tract. The second respiratory tract model may also be a 3D model of the patient's respiratory tract.

In one embodiment, the computation module uses a grayscale or numerical-value comparison method to acquire the position and shape of the patient's respiratory tract from the second tomographic image, in order to establish the second respiratory tract model according to the position and shape acquired.

To carry out the step of performing the second respiration simulation (S60) as shown in FIG. 1, the computation module performs respiration simulation on the second respiratory tract model to obtain data related to the patient's state of respiration while the patient is holding the occlusal structure between his or her teeth, such as a second respiratory pressure distribution, a second pressure difference, and a second jet angle.

To carry out the step of calculating the adjustment distance (S70) as shown in FIG. 1, the computation module calculates a corrective advancement distance based on the first respiratory pressure distribution, the first pressure difference, the first jet angle, the second respiratory pressure distribution, the second pressure difference, and the second jet angle.

The computation module may use an interpolation method, an extrapolation method, an averaging method, or a database comparison method to derive the corrective advancement distance from the first respiratory pressure distribution, the first pressure difference, the first jet angle, the second respiratory pressure distribution, the second pressure difference, and the second jet angle.

To carry out the step of adjusting the snoring mouthpiece (S80) as shown in FIG. 1, the computation module adjusts the patient's snoring mouthpiece according to the corrective advancement distance obtained from the previous step.

The step of adjusting the snoring mouthpiece (S80) may include advancing, or pulling outward, the mandible portion of the snoring mouthpiece, and the adjustment may be performed manually or by an adjustment device.

By implementing the method S100 of adjusting the snoring mouthpiece, the patient will have the snoring mouthpiece precisely adjusted. And because of that, the patient's teeth and tongue will be at the right positions, without hindering breathing or sleeping; moreover, snoring and the dangerous sleep apnea are effectively prevented.

The embodiments described above are intended only to demonstrate the technical concept and features of the present invention so as to enable a person skilled in the art to understand and implement the contents disclosed herein. It is understood that the disclosed embodiments are not to limit the scope of the present invention. Therefore, all equivalent changes or modifications based on the concept of the present invention should be encompassed by the appended claims.

What is claimed is:

1. A method of adjusting a snoring mouthpiece, comprising the steps of:

reading a first medical image, wherein a computation module reads a first tomographic image of a patient's respiratory tract;

establishing a first respiratory tract model, wherein the computation module establishes the first respiratory tract model according to the first tomographic image of the patient's respiratory tract;

performing a first respiration simulation, wherein the computation module performs respiration simulation on the first respiratory tract model to obtain a first respiratory pressure distribution, a first pressure difference, and a first jet angle;

reading a second medical image, wherein the computation module reads a second tomographic image of the patient's respiratory tract, and the second tomographic image of the patient's respiratory tract is taken while the patient is holding an occlusal structure between his or her teeth;

establishing a second respiratory tract model, wherein the computation module establishes the second respiratory tract model according to the second tomographic image of the patient's respiratory tract;

performing a second respiration simulation, where the computation module performs respiration simulation on the second respiratory tract model to obtain a second respiratory pressure distribution, a second pressure difference, and a second jet angle;

calculating an adjustment distance, wherein the computation module calculates a corrective advancement distance according to the first respiratory pressure distribution, the first pressure difference, the first jet angle, the second respiratory pressure distribution, the second pressure difference, and the second jet angle; and adjusting the snoring mouthpiece, wherein the computation module adjusts the snoring mouthpiece according to the corrective advancement distance.

2. The method of claim 1, wherein the first tomographic image of the patient's respiratory tract and the second tomographic image of the patient's respiratory tract are computed tomography (CT) images.

3. The method of claim 1, wherein the first tomographic image of the patient's respiratory tract and the second tomographic image of the patient's respiratory tract are cone-beam computed tomography (CBCT) images.

4. The method of claim 1, wherein the occlusal structure is a dental brace, an occlusal splint, an adjustable dental brace, or an adjustable occlusal splint.

5. The method of claim 1, wherein the step of establishing the first respiratory tract model comprises establishing a three-dimensional (3D) model of the patient's respiratory tract.

6. The method of claim 1, wherein the step of establishing the second respiratory tract model comprises establishing a three-dimensional (3D) model of the patient's respiratory tract.

7. The method of claim 1, wherein the corrective advancement distance is calculated by an interpolation method, an extrapolation method, an averaging method, or a database comparison method.

8. The method of claim 1, wherein the computation module is a computer system installed with at least one computation or application program, a microprocessor system, a personal computer, a laptop computer, or a smart device.

9. The method of claim 1, wherein the step of adjusting the snoring mouthpiece comprises advancing, or pulling outward, a mandible portion of the snoring mouthpiece.

10. The method of claim 1, wherein the step of adjusting the snoring mouthpiece is performed manually or by an adjustment device.

* * * * *